(12) United States Patent
Dawson et al.

(10) Patent No.: US 8,323,322 B2
(45) Date of Patent: Dec. 4, 2012

(54) MEDICAL IMPLANT FORMED FROM POROUS METAL AND METHOD

(75) Inventors: John M. Dawson, Chaska, MN (US); Adam Shinbrot, Golden Valley, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1460 days.

(21) Appl. No.: 11/868,315

(22) Filed: Oct. 5, 2007

(65) Prior Publication Data

US 2009/0093888 A1    Apr. 9, 2009

(51) Int. Cl.
*A61B 17/04*   (2006.01)
*A61B 17/86*   (2006.01)

(52) U.S. Cl. ........................................ 606/300; 606/310

(58) Field of Classification Search .......... 606/300–321; 623/17.11–17.16, 16.11, 23.3–23.31; 433/191–195, 433/200.1–206
See application file for complete search history.

(56) References Cited

U.S. PATENT DOCUMENTS

| | | | |
|---|---|---|---|
| 5,198,308 A | 3/1993 | Shetty et al. | |
| 5,282,861 A | 2/1994 | Kaplan | |
| 5,700,901 A | 12/1997 | Hurst et al. | |
| 6,241,771 B1 | 6/2001 | Gresser et al. | |
| 6,740,186 B2 | 5/2004 | Hawkins et al. | |
| 6,800,094 B2 | 10/2004 | Burkinshaw | |
| 6,926,903 B2 | 8/2005 | Pirhonen et al. | |
| 6,945,448 B2 | 9/2005 | Medlin et al. | |
| 6,974,625 B2 * | 12/2005 | Hunter et al. ............... | 428/304.4 |
| 6,976,999 B2 | 12/2005 | Charlebois et al. | |
| 7,150,879 B1 | 12/2006 | Lee et al. | |
| 7,238,186 B2 | 7/2007 | Zdeblick et al. | |
| 7,723,395 B2 * | 5/2010 | Ringeisen et al. ............... | 521/50 |
| 7,749,259 B2 * | 7/2010 | Lim et al. ....................... | 606/314 |
| 7,879,109 B2 * | 2/2011 | Borden et al. ............. | 623/23.76 |
| 7,883,661 B2 * | 2/2011 | Hamman et al. ................... | 419/2 |
| 7,892,261 B2 * | 2/2011 | Bonutti .......................... | 606/279 |
| 2004/0030341 A1 | 2/2004 | Aeschlimann et al. | |
| 2005/0055026 A1 | 3/2005 | Biedermann et al. | |
| 2005/0277928 A1 | 12/2005 | Boschert | |
| 2006/0121084 A1 * | 6/2006 | Borden et al. ................. | 424/426 |

(Continued)

FOREIGN PATENT DOCUMENTS

EP    0441123 A1    8/1991

(Continued)

OTHER PUBLICATIONS

Zimmer Spine, Inc., Puros Accugraft ALIF Allograft Surgical Technique, Aug. 2004, pp. 1-15, USA.

(Continued)

*Primary Examiner* — Thomas Barrett
*Assistant Examiner* — Matthew Lawson
(74) *Attorney, Agent, or Firm* — Seager Tufte & Wickhem LLC

(57) ABSTRACT

Medical implants are formed at least in part from porous metal wherein the pores of the metal are filled with a hardenable material. The hardenable material can be used to assist in the manufacture of the implant, permitting detailed machining of the implant. Further, the hardenable material can be a resorbable material that strengthens the implant during implantation but is resorbed, once implanted, to permit bone growth and infiltration. Further, in an alternate embodiment, the hardenable material can be a thermoplastic material that can be heated by ultrasonic energy to create an adhesive bond between a fastener and bone structure.

14 Claims, 3 Drawing Sheets

U.S. PATENT DOCUMENTS

2007/0111165 A1* 5/2007 Wallick et al. .............. 433/212.1

FOREIGN PATENT DOCUMENTS

WO         0071083 A1    11/2000
WO    2007/130648 A2    11/2007

OTHER PUBLICATIONS

Zimmer Spine, Inc., Puros Allografts Reference Guide, Product Information, Nov. 2004, 4 pages, USA.

Zimmer Spine, Inc., Puros Accugraft ALIF Allograft System, Three-In-One Solution, 2005, 4 pages, USA.

Zimmer Spine, Inc., Puros Cervical Specialty Allograft, A New Angle on Strength and Consistency, 2005, 4 pages, USA.

Zimmer Spine, Inc., Puros Symmetry PLIF Allograft System, Cortical Consistency Side-to-Side, 2005, 4 pages, USA.

* cited by examiner

MEDICAL IMPLANT FORMED FROM POROUS METAL AND METHOD

FIELD OF THE INVENTION

The present invention relates to medical implants and particularly to medical implants having a porous metal portion.

BACKGROUND OF THE INVENTION

Porous metals have been used extensively in medical implants. As disclosed in U.S. Pat. No. 5,282,861, these porous metal members permit bone growth into the pores, which, in turn, binds the implant to the bone.

The general nature of the porous metal provides some difficulties. The porous metal can be easily bent or distorted while being implanted, especially if the implant is hollow or very thin. For example, twisting forces developed during insertion may shear a screw in half even though the screw may have adequate strength for in situ loads. Further, the nature of the metal makes it difficult to machine certain fine parts from the porous metal. In particular, threaded fasteners are difficult to machine from the porous metal.

SUMMARY OF THE INVENTION

The present invention is premised on the realization that porous metal members that are part of medical implants can be strengthened by incorporating into the pores of the porous metal a hardening material. The hardening material strengthens the implant and allows it to be easily processed, e.g., machined.

In one embodiment, the hardening material is a resorbable material, which, once implanted, is resorbed allowing bone growth within the metal. In another embodiment, the hardening material is a resorbable material, which, once implanted, is resorbed and incorporated into the mineral matrix of ingrowth bony tissue.

The hardening material can further be various polymers that can be removed prior to implantation, or, alternatively, in situ, to form an adhesive bond once implanted.

The objects and advantages of the present invention will be further appreciated in light of the following detailed description and drawings in which:

DETAILED DESCRIPTION

According to the present invention, a medical implant such as a spinal implant or an orthopedic implant is formed at least in part from a porous metal member wherein the pores of the porous metal member are filled with a hardening material, which facilitates fabrication and/or implantation of the medical implant.

For use in the present invention, any biologically acceptable porous metal can be used. These can be formed from tantalum, titanium, zirconium, cobalt, chrome and stainless steel, as well as alloys of these. Preferably the pores of the porous metal will have a pore size of about 150 microns to about 500 microns, or more, depending upon the particular application. However, in certain applications a smaller pore size may be preferred.

One preferred porous metal is Trabecular Metal™ material, which is a porous tantalum material marketed by Zimmer Spine, Inc., of Edina, Minn. This material is also described in several U.S. patents, including, for example, U.S. Pat. Nos. 5,282,861; 5,443,515; and 6,063,442, the disclosures of which are incorporated herein by reference. These patents describe formation of a tantalum porous structure by chemical vapor deposition of tantalum onto a foam carbon structure.

Figure 1:
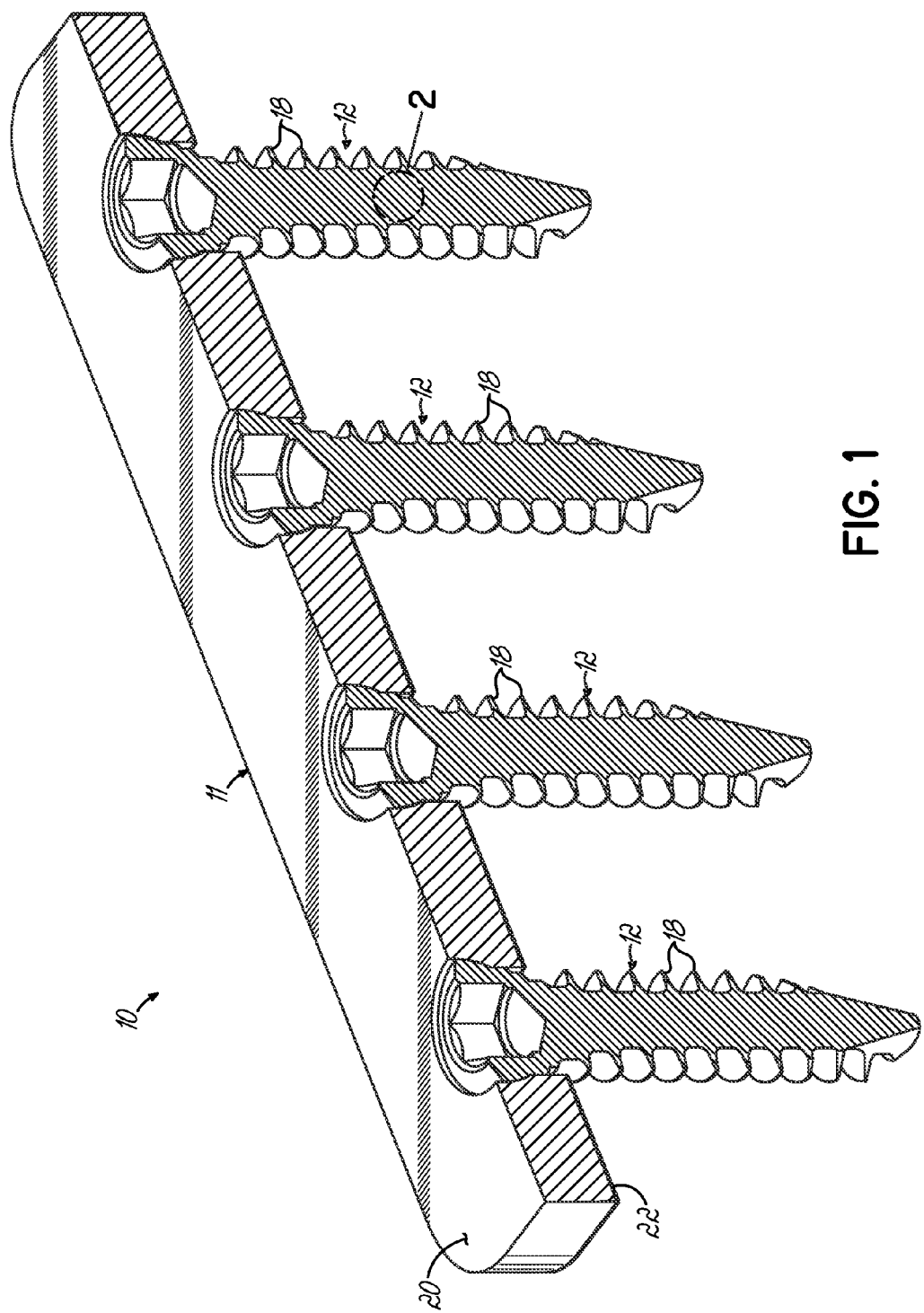
FIG. 1 is a cross section of an exemplary implant incorporating porous metal.

The porous metal member can be part of any medical implant. FIG. 1 shows an exemplary embodiment of a medical implant 10 made according to the present invention. Implant 10 includes a thin plate 11 and a plurality of fasteners, such as screws 12, with the plate 11 and fasteners 12 all formed from porous metal, preferably the porous tantalum previously discussed. The porous metal member can also be a nonthreaded fastener such as the fastener 14 shown in FIG. 3, or virtually any other implanted structure.

The hardenable material, which fills the pores at least on the surface of the porous metal member, can be ceramic, or a polymer, or a composite of a polymer and a ceramic, a composite of ceramics or a blend of polymers. In one preferred embodiment, the hardenable material is a resorbable material, which, once implanted within the body, is resorbed allowing bone growth into the pores.

There are many well known resorbable polymers. Particularly polymers formed from lactic acid and glycolic acid are suitable for use in the present invention. Specific resorbable materials include polylactic acid (PLA), polyglycolic acid (PGA), poly-L-lactide (PLLA), poly-DL-lactide (PDLLA), copolymers of PLA and PGA (PLGA), copolymers of PLLA and PDLLA. Other resorbable materials include resorbable hydrogels of poly(ethylene oxide), as well as methyl cellulose, hyaluronic acid, chitosan, collagen, gelatin, fibrin, dextran, agarose and carboxy methyl cellulose. The resorbable material can also be a composite of resorbable polymers with calcium sulfate, calcium phosphate, calcium phosphate cements, hydroxyapatite, beta-tricalcium phosphate and bioactive glass and glass ceramics. The resorbable materials can also be a ceramic including dicalcium phosphate dihydrate, calcium phosphate cements, hydroxyapatite, beta tricalcium phosphate, and bioactive glass and glass ceramics. Preferred polymers include poly (L-lactide), polyglycolic acid, polylactic acid and poly (L-lactide-co-glycolide).

The different resorbable materials have different rates of resorption, allowing the implant to be designed for the particular application requirements. The surgeon can select the bioresorbable material in the porous implant based on the resorption characteristics of the bioresorbable material. Quick resorption may be required when implanting forces are greater than physiological loads. Slower resorption is preferred if implant strength must be maintained during osteointegration. The filler can also be doped with osteoinductive or osteoconductive agents, antibiotics, or agents to enhance integration.

Alternately, nonresorbable polymers can be used such as thermoplastic or thermoset polymers, particularly polymers that can be softened subsequent to implantation using application of ultrasonic energy, light or heat. It may also be preferred to infiltrate the pores of the porous member with other harder polymers, such as the polyarylether ketone family of polymers, to provide strengthening for various portions of the porous metal member as discussed hereinafter. Other polymers may be infused into the porous metal to facilitate fabrication. These can be removed through solvent leaching prior to implantation.

The hardenable material can be infused into a porous metal member using a variety of different methods, either before or after forming the porous metal member. Thermoplastic polymers can be injection molded into the porous metal part by placing the porous metal into a mold and injecting a flowable material into the mold (i.e., insert molding). The porous metal part can be prepared by curing thermoset monomers with the assistance of initiators. The porous metal part can also be immersed in a molten solution or slurry of the hardening material. Many of the hardening materials are pastes. These can be pressed into the pores and allowed to set.

Figure 2:
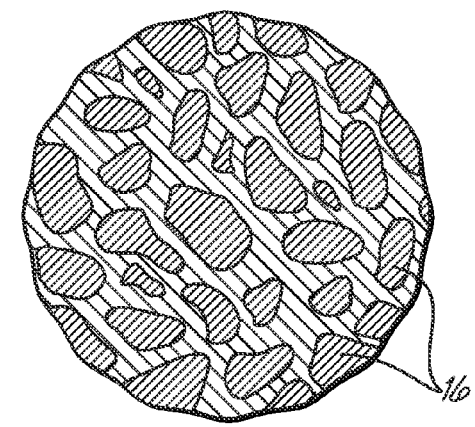
FIG. 2 is an enlarged cross sectional segment taken at circle 2 of FIG. 1.

To form fasteners, such as screws 12 shown in FIG. 1, a cylinder of porous metal is formed and infiltrated with a hardening material 16 (as shown in FIG. 2). In this embodiment the hardening material can be any material that can saturate the pores, provide strength to the overall porous metal composite, and can subsequently be removed either through resorption or through other processes. After the voids in the porous metal cylinder are filled with the desired hardening material 16, the threads 18 are machined in the cylinder to form screw 12. If the hardening material is a resorbable material, it will be left in the screw. If the hardening material is not resorbable, it may be removed prior to implantation.

Other machining and forming processes, such as grinding, shaping, bending, milling, and the like, can also be used to form an implant or part from a porous metal member filled with a hardened filler.

The plate 11 of implant 10 is also formed from a porous metal material. The plate 11 is first cut to shape and subsequently is filled with a resorbable hardening material such as the PLA, PLLA, PGA, a calcium phosphate material, or a blend or composite of them. Again, the pores are simply infused with the hardenable material, which is allowed to harden either through cooling or evaporation, and the implant 10 is then ready for implantation. Subsequent to implantation, the hardening material will resorb into the body and bone growth will replace the hardening material.

The pores in the plate 11 may be filled with a different resorbable material than the pores in the screws 12. For example, the plate 11 may be filled with a rapidly resorbable material, whereas the screws 12 are filled with a filler that is resorbed more gradually. Different portions of plate 10 may also be filled with different fillers. For example, a first side 20 of plate 10 may be filled with a first filer such as calcium phosphate and the second side 22 can be filled with PLA or even a thermoset polymer that is not resorbed.

Figure 3:
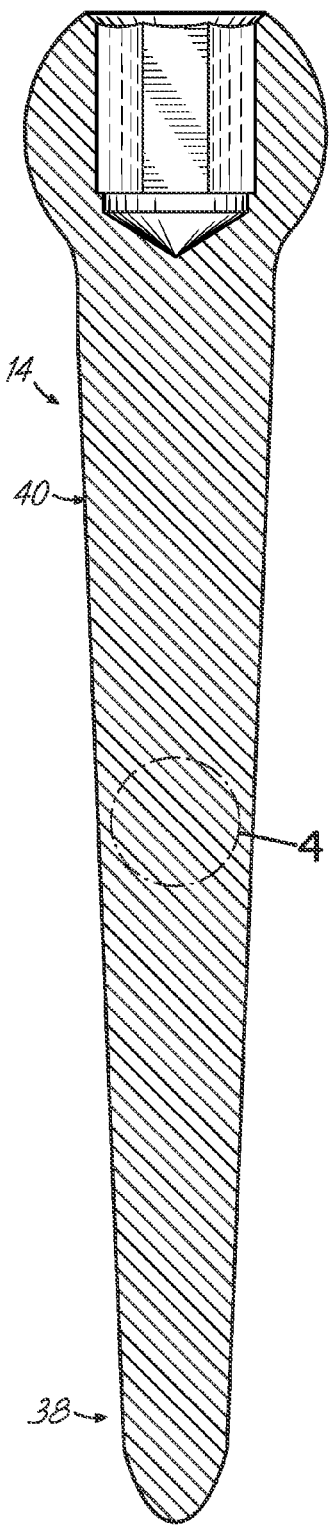
FIG. 3 is a cross section of a fastener formed from porous metal.
Figure 4:
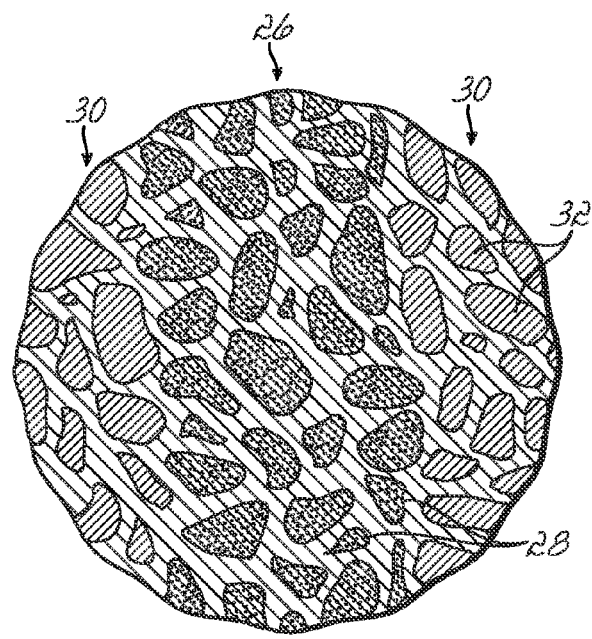
FIG. 4 is an enlarged cross sectional segment taken at circle 4 of FIG. 3.

FIGS. 3 and 4 show a further alternate embodiment of the present invention. In this embodiment, fastener 14, such as one that might be used in a spinal implant fixation assembly to attach a rod to a spinal column, as disclosed in Boschert published US application US2005/0277928, the disclosure of which is hereby incorporated by reference, is formed from a porous metal. This is merely an exemplary fastener.

In this embodiment, the fastener 14 is a tapered cylinder formed from the porous metal. Alternately, the fastener 14 can have a nontapered shape such as a cylinder or rectangle. As shown in FIG. 4, two separate materials are used to fill the pores of the porous metal. The interior portion 26 of the porous metal is formed with a very hard polymer 28, which is intended to remain in place and provide strength to the fastener 14. Any biologically acceptable polymer having the desired physical characteristics can be employed. One particular polymeric material suitable for use in the present invention is polyetheretherketone.

The pores in the outer portion 30 of the fastener 14 are filled with a polymeric material 32 which can be applied by localized application of energy such as ultrasonic, light, or thermal energy. Any biologically acceptable thermoplastic adhesive can be used. One suitable polymeric material is polyethylene.

This fastener 14 can be filled with the hardening materials 28 and 32 in a variety of different manners. The inner, harder, polymeric material 28 can be injected through a central shaft (not shown) drilled through the fastener, or, alternately, the entire structure can be impregnated with the material 28 and, subsequently, the outer portion of the material removed by immersing fastener 20 for a period of time in a suitable solvent to dissolve the polymer 28 from the outer portion 30 of the fastener 14.

The softer polymer 32 on the outer surface 30 would then simply be applied by immersing the fastener 14 in the softer polymer either as a solution or as a melt. The polymer can be one which changes its physical state upon application of energy.

Figure 5:
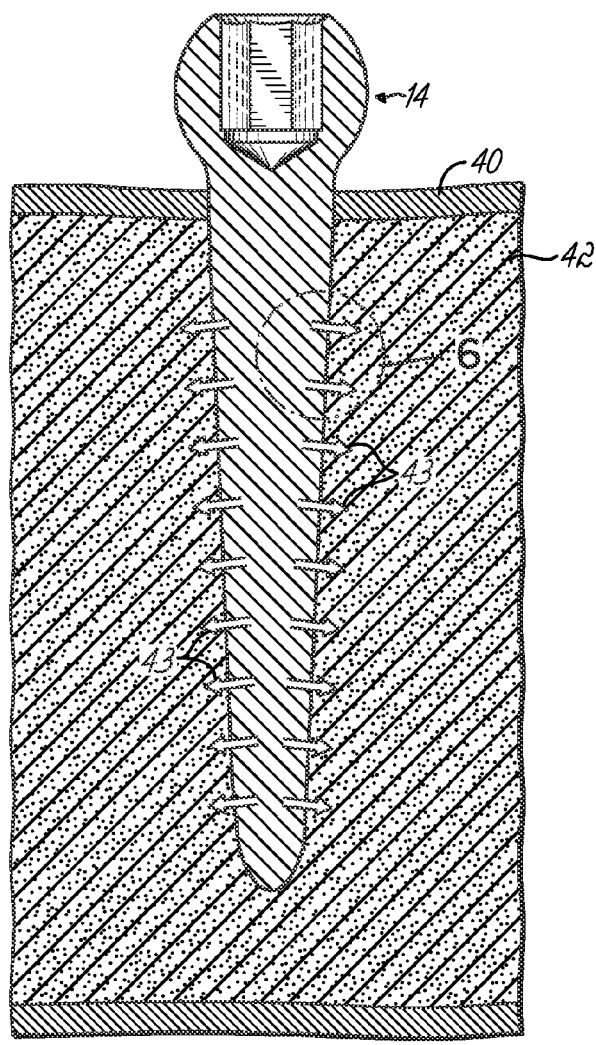
FIG. 5 is a diagrammatic cross section of an implanted fastener.
Figure 6:
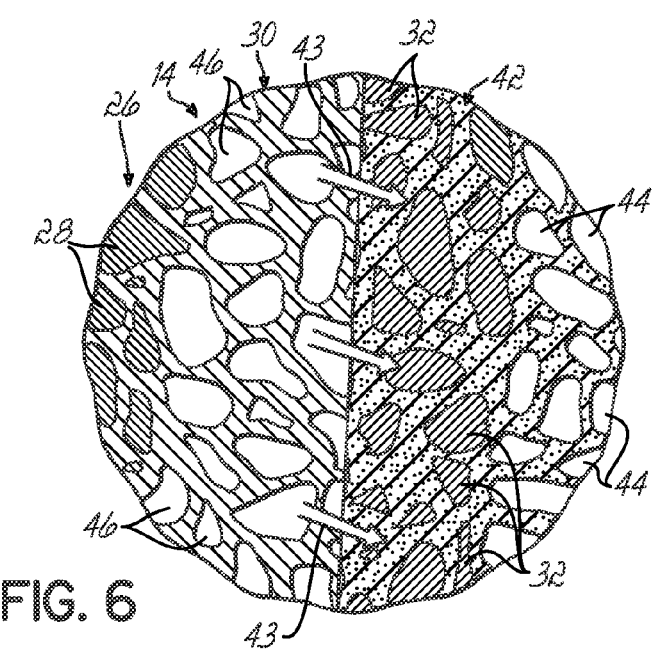
FIG. 6 is an enlarged cross sectional segment taken at circle 6 of FIG. 5.

Referring to FIGS. 5 and 6, the fastener 14 can be implanted in a unique manner. In particular, the fastener would be inserted in a hole which extends through the cortical bone 40 and into the cancellous bone 42. Fastener 14 would then be subjected to energy, for example, to ultraviolet, ultrasonic, or thermal energy to cause the outer polymeric material 32 in pores of fastener 14 to melt. The polymeric material would flow as indicated by arrows 43, forming a bond by causing at least a portion of the polymeric material 32 to flow into pores 44 in cancellous bone 42. This would leave open pores 46 remaining within the fastener 14, which may be subsequently filled with new bone growth.

This structure will provide a stronger fastener because of the inner polymeric material or filler 28 in inner portion 26, and will provide a stronger bond to the bone because of the coupling activity of the softer polymeric material 32 which flows from the outer peripheral portion 30 of the porous metal into the porous cancellous bone 42.

In another embodiment, the inner portion of the fastener can be solid, non-porous material, such as a metal, and the porous material can be coupled to the outer surface of the solid core through a coating/adhesion process. The porous outer portion of the fastener can then be infused with the bioresorbable polymer.

Alternatively, two different resorbable materials could be used in the fastener 14. The inner material may be one that is resorbed at a different rate than the outer material.

Further, porous metal fastener 14 can be formed with a lower pointed portion 38 filled with a first filler and an upper portion 40 filled with a second filler.

The first filler can be an ultrasonically meltable polymer or a rapidly resorbed filler. The second filler may be a thermoset polymer or a resorbable filler. If the first and second fillers are resorbable, it may be desirable for the first filler to resorb quickly to promote rapid bone infusion. The second filler may be a slowly resorbed filler that mains the strength of the fasteners.

Using multiple hardening fillers allows the porous metal part, in this case a fastener, to be specifically engineered to suit a particular application. Different hardenable materials can be employed as needed to provide for machining prior to implantation, short term or long term strength during implantation, or to provide adhesion or a combination of these.

These different embodiments have all been described, as well as the preferred method of practicing the present invention. However, the invention itself should only be defined by the appended claims.

What is claimed is:

1. A medical implant including a porous metal member, said porous metal member including a plurality of pores wherein pores of an inner portion of the implant are filled with a first resorbable hardening material, and pores of an outer portion of the implant are filled with a second hardening material different from the first hardening material, the first hardening material being harder than the second hardening material, wherein said first resorbable hardening material is a polymer.

2. The medical implant claimed in claim 1 wherein said first resorbable hardening material is a thermoplastic polymer.

3. The medical implant claimed in claim 1 wherein said second hardening material is a second resorbable material and wherein said first and second resorbable materials have different rates of resorption.

4. The medical implant claimed in claim 1 wherein said implant is a fastener and said second hardening material is a polymeric adhesive.

5. The medical implant claimed in claim 1 wherein said implant is a fastener.

6. The medical implant claimed in claim 1, wherein the medical implant is a fastener, the fastener including threads machined in the porous metal member.

7. A method of forming a medical implant comprising filling pores of an inner portion of a porous metal member with a first hardenable polymer material and filling pores of an outer portion of the porous metal member with a second resorbable hardenable polymer material, the first hardenable polymer material being harder than the second hardenable polymer material.

8. The method of claim 7 wherein said first hardenable polymer material is a resorbable material.

9. The method claimed in claim 8 wherein said second hardenable polymer material is a resorbable material, wherein the first and second resorbable hardenable polymer materials have different rates of resorption.

10. The method medical implant claimed in claim 7, wherein the first hardening hardenable polymer material is polyetheretherketone.

11. A method of inserting a fastener into bone comprising:
positioning a fastener in said bone wherein said fastener is a porous metal member having inner pores filled with a first hardening polymer material and outer pores filled with a second hardening polymeric material, wherein the first hardening material is harder than the second hardening polymeric material; wherein said second hardening polymeric material is resorbable;
altering said second hardening polymeric material causing said second hardening polymeric material to flow from outer pores of said porous member into said bone.

12. The method claimed in claim 11 wherein the step of altering the second hardening polymeric material comprises applying energy to the second hardening polymeric material thereby making said second hardening polymeric material flowable.

13. The method claimed in claim 12 wherein said energy is ultra violet light.

14. The method claimed in claim 11 wherein an opening is formed in said bone and said fastener is positioned in said opening.

* * * * *